(12) United States Patent
Liu et al.

(10) Patent No.: US 7,243,549 B2
(45) Date of Patent: Jul. 17, 2007

(54) ACOUSTIC WAVE LUBRICITY SENSOR

(75) Inventors: James ZT Liu, Belvidere, IL (US);
Michael L. Rhodes, Richfield, MN (US); Aziz Rahman, Sharon, MA (US)

(73) Assignee: Honeywell International Inc., Morristown, NJ (US)

( * ) Notice: Subject to any disclaimer, the term of this patent is extended or adjusted under 35 U.S.C. 154(b) by 204 days.

(21) Appl. No.: 11/132,870

(22) Filed: May 19, 2005

(65) Prior Publication Data
US 2006/0260404 A1    Nov. 23, 2006

(51) Int. Cl.
*G01N 29/00* (2006.01)
*G01M 3/04* (2006.01)

(52) U.S. Cl. .............. 73/592; 73/40.5 A; 73/53.05; 73/54.1

(58) Field of Classification Search ............. 73/592, 73/53.05, 54.1, 61.44, 53.04, 54.01, 54.02, 73/61.41, 43.05 A; 310/367, 361, 368
See application file for complete search history.

(56) References Cited

U.S. PATENT DOCUMENTS

| | | | | |
|---|---|---|---|---|
| 4,418,299 A | | 11/1983 | Momosaki ............. 310/361 |
| 4,900,971 A | | 2/1990 | Kawashima ............ 310/361 |
| 5,789,665 A | * | 8/1998 | Voelker et al. ........... 73/53.05 |
| 6,247,905 B1 | | 6/2001 | Dohner .................. 417/322 |
| 6,669,454 B2 | * | 12/2003 | Lal et al. ................ 417/410.2 |
| 6,688,158 B2 | | 2/2004 | Cunningham et al. ...... 73/24.06 |
| 6,837,097 B2 | | 1/2005 | Cunningham et al. ...... 73/24.06 |
| 6,851,297 B2 | | 2/2005 | Cunningham et al. ...... 73/24.06 |
| 6,877,360 B1 | * | 4/2005 | Discenzo ................. 73/53.05 |
| 7,134,323 B1 | * | 11/2006 | Discenzo ................. 73/53.05 |
| 2002/0178780 A1 | * | 12/2002 | Van Mullekom et al. .... 73/10 |
| 2003/0196479 A1 | * | 10/2003 | Kasen et al. .............. 73/53.05 |
| 2005/0009712 A1 | | 1/2005 | Erdemir .................. 508/156 |
| 2005/0016262 A1 | | 1/2005 | Webster .................. 73/53.06 |
| 2005/0067920 A1 | | 3/2005 | Weinberg et al. ......... 310/313 R |
| 2005/0072217 A1 | | 4/2005 | Discenzo ................. 73/53.05 |
| 2005/0247289 A1 | * | 11/2005 | Visser et al. ............. 123/406.47 |

FOREIGN PATENT DOCUMENTS

WO    WO 2004/007648 A1    1/2004

\* cited by examiner

*Primary Examiner*—Hezron Williams
*Assistant Examiner*—Jacques M. Saint-Surin
(74) *Attorney, Agent, or Firm*—Kermit D. Lopez; Luis M. Ortiz

(57) ABSTRACT

A lubricity sensor includes a flexural plate wave device and a face shear mode bulk acoustic wave device, which is associated with and located proximate to the flexural plate wave device. The face shear mode bulk acoustic wave device and the flexural plate wave device form a lubricity sensor wherein acoustic wave data produced by the flexural plate device together with the face shear mode bulk acoustic wave device when the lubricity sensor is exposed to a liquid relates directly to a lubricity of the liquid thereby providing lubricity measurement data associated with the liquid. The acoustic wave data can comprises the oscillation gain compensation, the frequency, amplitude and/or phase velocity associated with the flexural plate device and the shear mode bulk acoustic wave device such that the oscillation gain compensation, the frequency, amplitude and/or phase velocity provide an indication of the lubricity of the liquid.

20 Claims, 3 Drawing Sheets

Face Shear

ACOUSTIC WAVE LUBRICITY SENSOR

TECHNICAL FIELD

Embodiments are generally related to sensing devices and components thereof. Embodiments also relate to lubricity sensors. Embodiments additionally relate to acoustic wave devices. Embodiments specifically relate to piezoelectric devices, including flexural plate wave (FPW) and face shear mode (FSM) devices and components.

BACKGROUND OF THE INVENTION

Acoustic wave sensors are utilized in a variety of sensing applications, such as, for example, temperature and/or pressure sensing devices and systems. Acoustic wave devices have been in commercial use for over sixty years. Although the telecommunications industry is the largest user of acoustic wave devices, they are also used for sensor applications, such as in chemical vapor detection. Acoustic wave sensors are so named because they use a mechanical, or acoustic, wave as the sensing mechanism. As the acoustic wave propagates through or on the surface of the material, any changes to the propagation path affect the characteristics of the wave.

Changes in acoustic wave characteristics can be monitored by measuring the frequency or phase characteristics of the sensor and can then be correlated to the corresponding physical quantity or chemical quantity that is being measured. Virtually all acoustic wave devices and sensors utilize a piezoelectric crystal (e.g., quartz), a semi-crystalline piezoelectric materials (e.g., PVDF), or an amorphous piezoelectric materials to generate the acoustic wave. Three mechanisms can contribute to acoustic wave sensor response, i.e., mass-loading, visco-elastic and acousto-electric effect. The mass-loading of chemicals alters the frequency, amplitude, and phase and Q value of such sensors. Most acoustic wave chemical detection sensors, for example, rely on the mass sensitivity of the sensor in conjunction with a chemically selective coating that absorbs the vapors of interest resulting in an increased mass loading of the acoustic wave sensor.

Examples of acoustic wave sensors include acoustic wave detection devices, which are utilized to detect the presence of substances, such as chemicals, or environmental conditions such as temperature and pressure. An acoustical or acoustic wave (e.g., SAW/BAW) device acting as a sensor can provide a highly sensitive detection mechanism due to the high sensitivity to surface loading and the low noise, which results from their intrinsic high Q factor. Surface acoustic wave devices are typically fabricated using photolithographic techniques with comb-like interdigital transducers placed on a piezoelectric material. Surface acoustic wave devices may have either a delay line or a resonator configuration. Bulk acoustic wave devices are typically fabricated using a vacuum plater, such as those made by CHA, Transat or Saunder. The choice of the electrode materials and the thickness of the electrode are controlled by filament temperature and total heating time. The size and shape of electrodes are defined by proper use of masks.

Surface acoustic wave resonator (SAW-R), surface acoustic wave delay line (SAW-DL), surface transverse wave (STW), bulk acoustic wave (BAW), flexural plate wave (FPW), and acoustic plate mode (APM) all can be utilized in various sensing measurement applications. One of the primary differences between an acoustic wave sensor and a conventional sensor is that an acoustic wave sensor can store energy mechanically. Once such a sensor is supplied with a certain amount of energy (e.g., through RF), the sensor can operate for a time without any active part (e.g., without a power supply or oscillator). This feature makes it possible to implement an acoustic wave sensor in an RF powered passive and wireless sensing application.

One field where acoustic wave devices may offer a promising future is the area lubricity measurements. Lubricity is an important quality factor for diesel fuels due to the reduction lubricity associated with the extreme hydrogenation needed to obtain the low sulfur levels required in modern diesel fuels. In general, diesel engines rely on fuel as a lubricant for their internal moving components. The lubricity of the fuel affects the wear between two metal parts that are in contact. Wear due to the friction between these parts will cause failure of the components if there is insufficient lubricity. The use of a high lubricity fuel may reduce the wear and increase component life.

Sulfur is found naturally in crude oil and carries through into diesel and gasoline fuels unless specifically removed through distillation. As a result, diesel and gasoline fuels used in engines may contain sulfur in concentrations up to 3000 parts per million (ppm). At such high concentrations, sulfur provides high lubricity in fuel pumps and injector systems that deliver the fuel to the combustion chamber in an engine. Fuel sulfur, however, also causes polluting emissions, particularly $SO_2$ and soot particles, and poisons the advanced emission-control and after treatment devices that are being developed to enable diesel engines to meet progressively more stringent emissions standards. Sulfur dioxide emissions are associated with environmental problems such as acid rain. However, when the current sulfur level is reduced in fuels, high friction and wear occur on sliding surfaces of fuel delivery systems and cause catastrophic failure.

Fuels with lower sulfur content have lower lubricity compared to those with higher sulfur content. Thus, low-sulfur diesel fuels do not provide sufficient lubricity for use in diesel engines, and the use of low-sulfur diesel fuels results in high friction and catastrophic wear of fuel pumps and injectors. When lubricity is compromised, wear increases in fuel injection systems, most of which were originally designed with the natural lubricating properties of traditional diesel fuel in mind.

The lower lubricity of low-sulfur fuels poses significant problems for producers as well as for end-users of diesel fuels. Reduction in lubricity also contributes to a loss in usable power due to the increased friction the engine has to overcome. Because fuels with lower sulfur contents exhibit increased friction characteristics compared to fuels with higher sulfur contents, a perfectly tuned engine experiences a noticeable drop in efficiency when the fuel is changed from a high-sulfur fuel to a low-sulfur fuel.

Traditional lubricity is tested by utilizing the Scuffing Load Ball on Cylinder (SLBOCLE) and the High Frequency Reciprocating Rig Test (HFRR) methods. In general, the SLBOCLE test measures the maximum load a ball on rotating cylinder can sustain without experiencing scuffing wear. In the HFRR testing technique, a hardened steel ball can oscillate across a hardened steel plate under a fixed load for a particular amount of time (e.g., 75 minutes). The point of contact between the ball and plate is immersed in a sample. The size of the resulting wear scar on the steel ball is a measure of the sample's lubricity. Such testing methodologies are large, expensive and time-consuming.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved sensing device.

It is another aspect of the present invention to provide for an improved acoustic wave sensing device It is yet another aspect of the present invention to provide for a lubricity sensor.

It is a further aspect of the present invention to provide for a lubricity sensor based on acoustic wave sensing components, particularly flexural plate wave (FPW) and face shear mode (FSM) devices.

The aforementioned aspects and other objectives and advantages can now be achieved as described herein. A lubricity sensor is disclosed, which includes a flexural plate wave device and a face shear mode device, which is associated with and located proximate to the flexural plate wave device. The face shear mode device and the flexural plate wave device form a lubricity sensor wherein acoustic wave data produced by the flexural plate device together with the face shear mode device when the lubricity sensor is exposed to a liquid relates directly to a lubricity of the liquid thereby providing lubricity measurement data associated with the liquid. The acoustic wave sensor data can comprises the frequency, the amplitude and/or phase velocity associated with the flexural plate device and the shear mode device such that the frequency, the amplitude and/or phase velocity provide an indication of the lubricity of the liquid.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
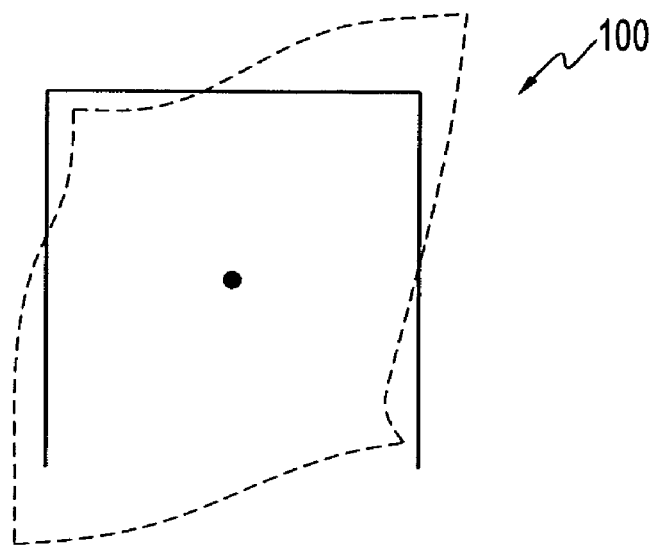
FIG. 1 illustrates a face shear mode (FSM) bulk acoustic wave (BAW) device in accordance with an embodiment.

FIG. 1 illustrates a face shear mode (FSM) 100 in accordance with an embodiment. FSM configuration 100 is based on the concept of face shear inherent with quartz resonators in the context of piezoelectricity. In general, quartz resonator units perform their oscillating operation based on the piezoelectric effect of single quartz crystal. Such devices can provide very stable oscillation at a constant frequency. Such a quartz resonator can be provided as an AT-cut quartz element. FSM 100 can be produced by an CT or DT-cut quartz element based on the piezoelectric effect, which converts mechanical stress in such a crystal or CT or DT-cut quartz element into an electrical signal (e.g., voltage) and vice-versa. In this manner, the piezoelectric effect converts one or more electrical impulses to mechanical stress, which is generally subject to the very high Q mechanical resonances of the crystal and is in turn linked back into an electrical circuit.

The crystal vibrates in a number of manners, which is known as face shear mode (FSM), as illustrated by FSM 100 depicted in FIG. 1. One non-limiting example of an FSM device that can be adapted for use in accordance with one or more of the embodiments disclosed herein is described in U.S. Pat. No. 4,418,299, entitled "Face-Shear Mode Quartz Crystal Vibrators and Methods of Manufacture" which issued to Eishi Momasaki on Nov. 29, 1983 and which is incorporated herein by reference. Another example of an FSM device that can be adapted for use in accordance with one or more embodiments is described in U.S. Pat. No. 4,900,971, entitled "Face Shear Mode Quartz Crystal Resonator" which issued to Kawashima, et al on Feb. 13, 1990, and is incorporated herein by reference. Note that U.S. Pat. No. 4,418,299 and U.S. Pat. No. 4,900,971 are referenced herein for general edification and illustrative purposes only and are not considered limiting features of the embodiments. It can be appreciated that other types of FSM devices can be adapted for use with the embodiments disclosed herein.

Figure 2:
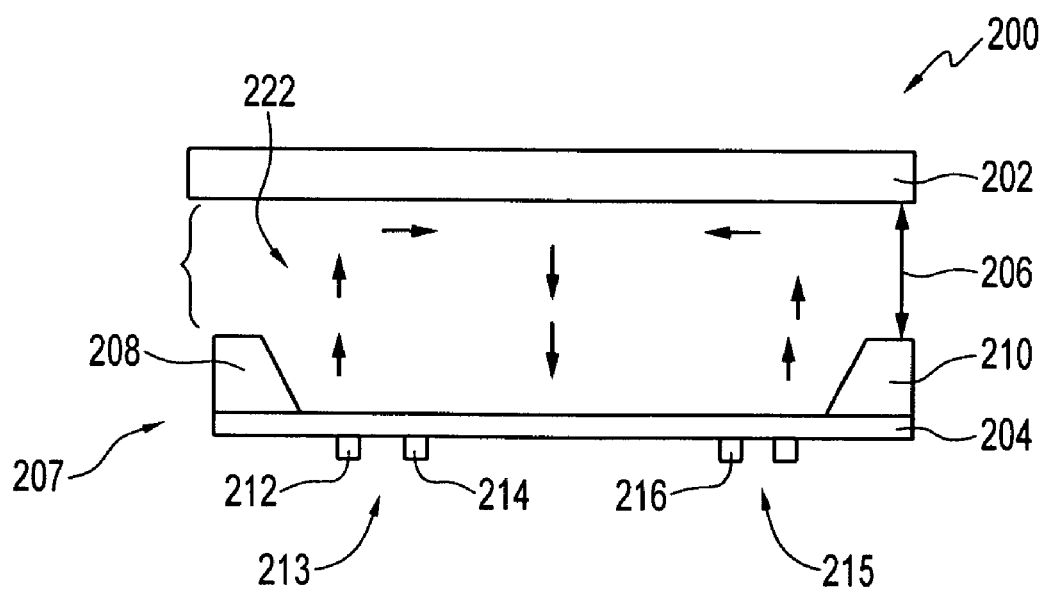
FIG. 2 illustrates a lubricity sensor, which can be implemented in accordance with a preferred embodiment.

FIG. 2 illustrates a lubricity sensor 200, which can be implemented in accordance with a preferred embodiment. Lubricity sensor 200 generally includes a flexural plate wave (FPW) device or component 207 that includes FPW portions 204, 208, which are formulated upon a piezoelectric substrate or plate 204 in association with two groups 213, 215 of respective interdigital transducers 212, 214 and 216, 218. A face shear mode (FSM) device or component 202 is positioned proximate to FPW device or component 207. By placing FPW device 207 and FSM device 202 close to one another, the lubricity sensor 200 can be formed. The amplitudes and/or phase velocity associated with the FPW device 207 and the FSM device 202 are directly related to the lubricity of a liquid flowing within a gap 223 between FSM device 202 and FPW device 207.

Note that the fluid flow direction of the liquid (e.g., diesel fuel) is indicated in FIG. 2 by arrows 222. Additionally, arrow 206 depicted in FIG. 2 indicates that the distance between FSM device 202 and FPW device 207 is preferably fixed. Lubricity sensor 202 can therefore provide an indication of the lubricity of a fluid, such as, for example, diesel fuel. Note that as utilized herein, the term "lubricity" can be defined as the property of a lubricant that causes a difference in friction under conditions of boundary lubrication when all the known factors except the lubricant itself are the same. Thus, the lower the friction the higher the lubricity.

Figure 3:
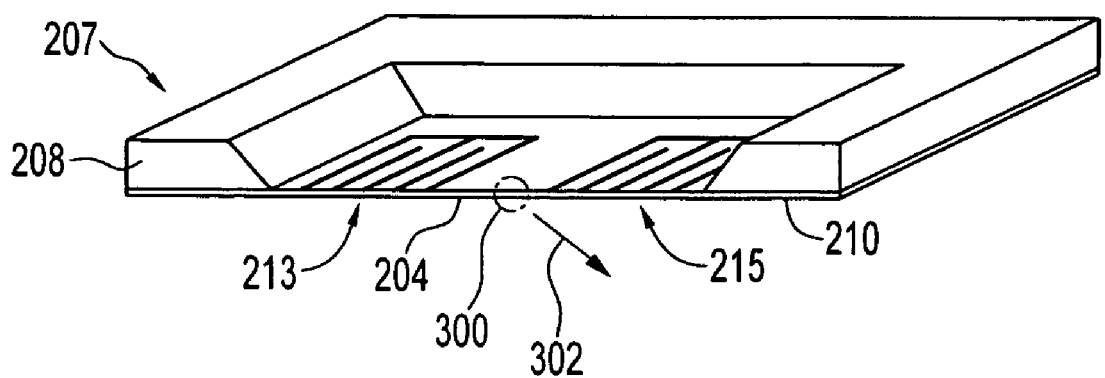
FIG. 3 and FIG. 3A illustrates a flexural plate wave (FPW) device, which can be adapted for use in accordance with the lubricity sensor depicted in FIG. 2.
Figure 3A:
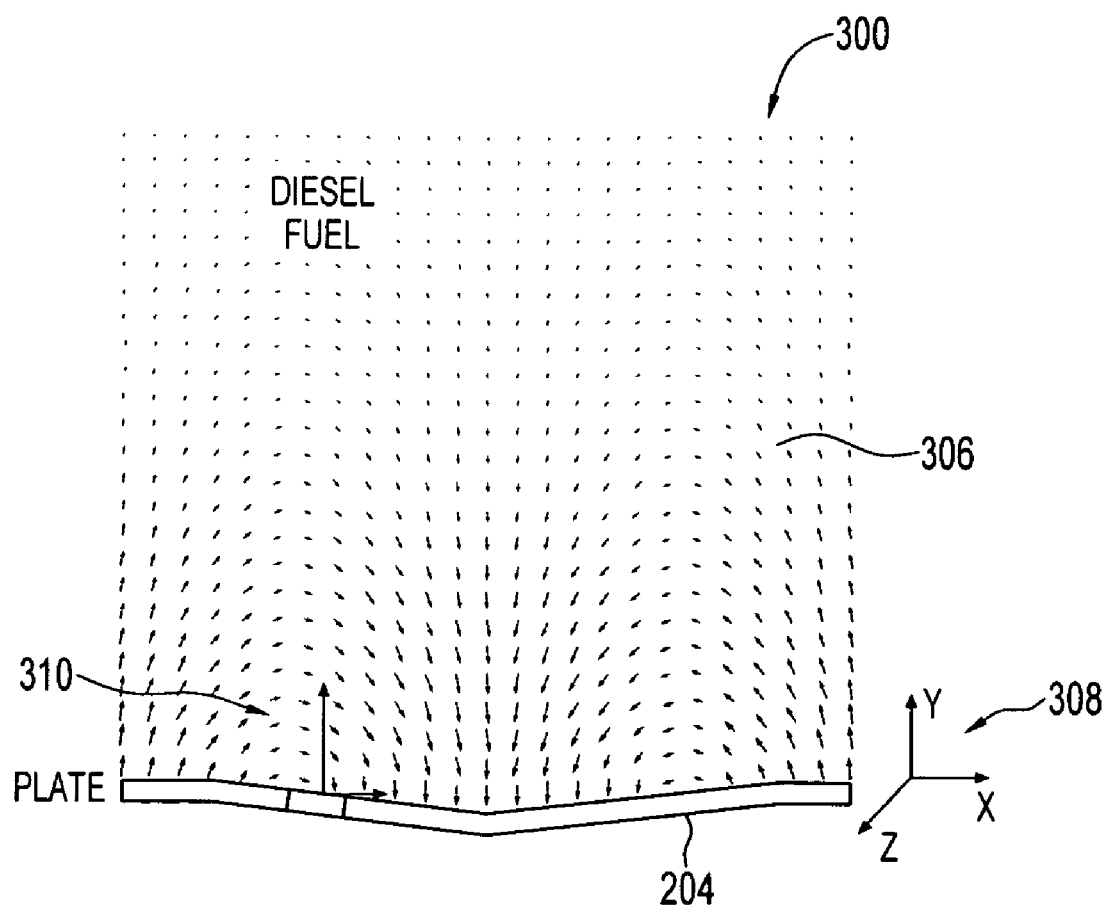

FIG. 3 and FIG. 3A illustrate a flexural plate wave (FPW) device 207, which can be adapted for use in accordance with the lubricity sensor 200 depicted in FIG. 2. Note that in FIGS. 2-3A, identical or similar parts or components are generally indicated by identical reference numerals. In FIG. 3A, for example, a portion 300 of FPW device 207 is shown in greater detail, including the fluid, in this case, diesel fuel 306 located proximate to the plate 204. X-Y-Z coordinates 308 are also provided in comparison to arrows 310, which provide an indication of the stress placed upon plate 204 by the diesel fuel 306 in order to assist the lubricity sensor 200 in determining the lubricity of the diesel fuel 306.

In FPW device 207, one or more acoustic waves can be excited in a thin membrane. An example of such a membrane is provided in FIG. 4 below as membrane 407. FPW device 207 can sense quantities that cause its phase velocity to change. A unique feature of FPW device 207 is that it can be dimensioned so that its phase velocity is lower than that of the phase velocity of most liquids, including the phase velocity of the diesel fuel 306. When FPW device 207 is utilized in a liquid, a slow mode of propagation can exist in which radiation does not emanate from plate 204. Therefore, FPW device 207 can function well as a chemical sensor with respect to diesel fuel 306.

Because the plate 204 of FPW device 207 can be as thin as a few μm, the sensitivity due to the mass loading is very high. Mass-loading causes the phase velocity of an acoustic wave propagating on the plate 204 to decrease. The amplitudes of the displacements associated with a flexural wave of a give total power are generally larger than other modes acoustic wave sensors. As a result of this large amplitude motion, FPW device 207 can be utilized as a sensor and actuator in "pumping" and mixing of fluids. An example of this "pumping" phenomenon is thus illustrated by the configuration depicted in FIGS. 3-3A. FPW device 207 can employ a number of interdigital transducers. Although only IDTS 212, 214 and 216, 215 are depicted in FIG. 2 with respect to FPW device 207, it can be appreciated that more IDTs may be utilized, depending upon design considerations. Such IDTs can be utilized by FPW device 207 in association with piezoelectric coupling to generate and detect waves.

FPW device 207 can be implemented as a delay-line oscillator. If it is desired to increase sensitivity, however, FPW device 207 can be configured thinner, thereby reducing the velocity (and incidentally reducing the frequency). This increased sensitivity with a lowered operating frequency is opposite to the situation of thickness shear mode (TSM), surface acoustic wave (SAW) and APM devices. The lubricity sensor 200 through the use of FPW device 207 has approximately ten times a higher sensitivity than that of, for example, an SH-APM sensor. The membrane motion can be normal to the surface (e.g., like that of a vibrating drumhead) or can propagate a shear wave like in SH-SAW devices.

Any perturbation of the surface changes the propagating wave velocity and damps the acoustic vibration. Because the FPW device 207 can be constructed on a silicon waver (e.g., see the silicon substrate 402 depicted in FIG. 4), large arrays of such devices can be fabricated on single substrates. Additionally, all drive and detection electronics can be integrated onto the same substrate. Note that for large scale sensor system integration, the FPW device 207 is only one of many acoustic technologies that might be implemented in the context of the lubricity sensor described herein.

Figure 4:
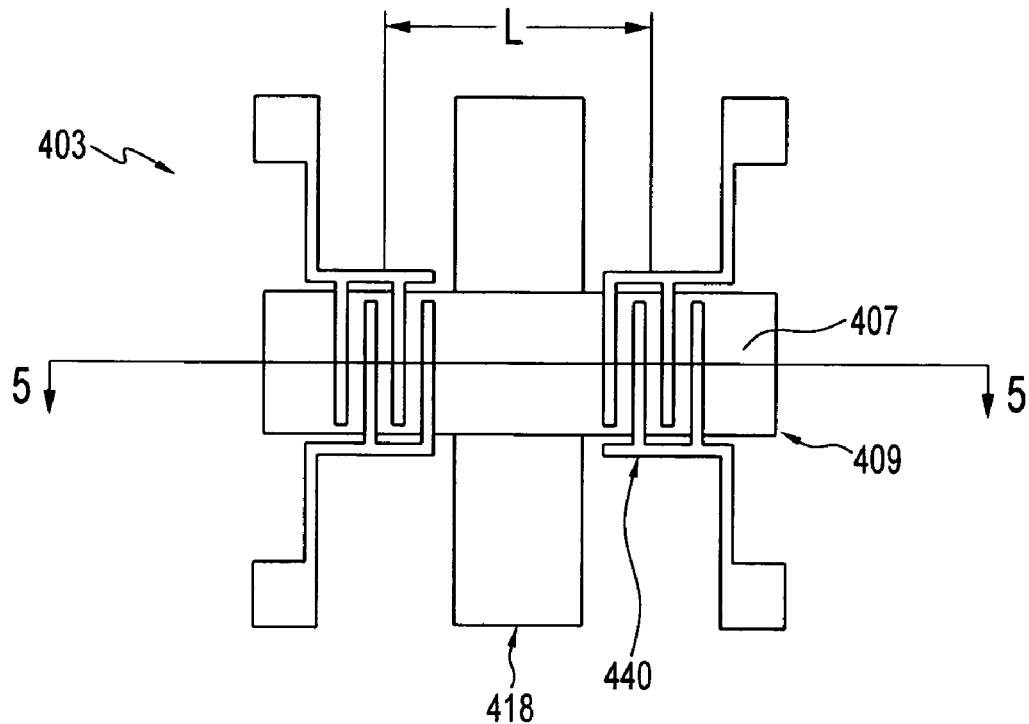
FIG. 4 illustrates a lubricity sensor, which can be implemented in accordance with an alternative embodiment.
Figure 5:
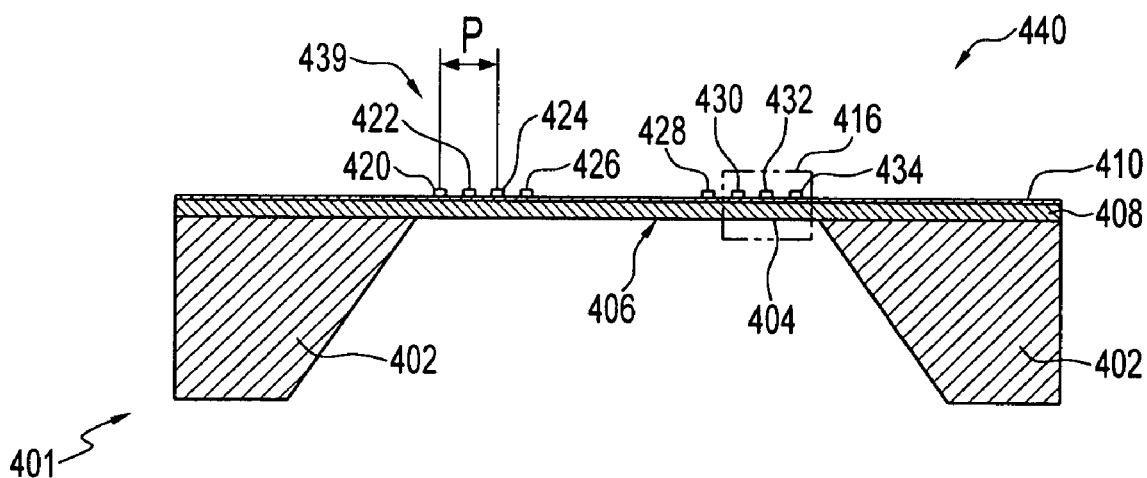
FIG. 5 shows side view 401 of sensor 400.

FIG. 4 illustrates a lubricity sensor 400, which can be implemented in accordance with an alternative embodiment. Sensor 400 can be implemented in the context of an FPW device, such as FPW device 207 depicted in FIG. 3. Note that lubricity sensor 400 is shown in FIG. 4 by a top view 403 and a side view 401 thereof in FIG. 5. Thus, top view 403 provides a top AA' sectional view, while side view 401 provides a cross-sectional AA' view of sensor 400. A perimeter 409 of a membrane 407 is depicted in the top view 403, while a substrate 402 is depicted in side view 401. A silicon nitride layer 408 can be formed upon substrate 402. A ZnO layer 410 can then be formed above the silicon nitride layer 408. Two groups 439, 440 of respective interdigital transducers 420, 422, 424, 426 and 428, 430, 432, 434 can also be formed above the ZnO layer 410. A metal ground plate 418 can also be provided in association with the two groups 439, 440 of respective interdigital transducers 420, 422, 424, 426 and 428, 430, 432, 434.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A lubricity sensor, comprising:
   a flexural plate wave device; and
   a face shear mode bulk acoustic wave device associated with and located proximate to said flexural plate wave device, wherein said face shear mode bulk acoustic wave device and said flexural plate wave device form a lubricity sensor wherein acoustic wave data produced by said flexural plate device together with said face shear mode bulk acoustic wave device when said lubricity sensor is exposed to a liquid relates directly to a lubricity of said liquid thereby providing lubricity measurement data associated with said liquid.

2. The sensor of claim 1 wherein said acoustic wave data comprises an amplitude associated with said flexural plate device and said shear mode device such that said amplitude provides an indication of said lubricity of said liquid.

3. The sensor of claim 1 wherein said acoustic wave data comprises a phase velocity associated with said flexural plate device and said shear mode device such that said phase velocity provides an indication of said lubricity of said liquid.

4. The sensor of claim 1 wherein said acoustic wave data comprises an amplitude and a phase velocity associated with said flexural plate device and said shear mode device such that said amplitude and said phase velocity together provide an indication of said lubricity of said liquid.

5. The sensor of claim 1 wherein said acoustic wave data comprises a frequency associated with said flexural plate device and said face shear mode bulk acoustic wave device such that said frequency provides an indication of said lubricity of said liquid.

6. The sensor of claim 1 wherein said acoustic wave data comprises an oscillation gain compensation associated with said flexural plate device and said face shear mode bulk acoustic wave device such that said oscillation gain compensation provides an indication of said lubricity of said liquid.

7. The sensor of claim 1 wherein said flexural plate device and said face shear mode bulk acoustic wave device each operation in a low operating frequency range of approximately 0.1 MHz to 100 MHz.

8. The sensor of claim 1 wherein said flexural plate wave device comprises a membrane in which at least one interdigital transducer (IDT) is formed upon in order to pump a flow of said liquid in a desired direction.

9. The sensor of claim 1 wherein said flexural plate wave device comprises a phase velocity that is lower than a phase velocity of said liquid.

10. The sensor of claim 1 wherein said liquid comprises oil.

11. The sensor of claim 1 wherein said liquid comprises diesel fuel.

12. The sensor of claim 1 wherein said flexural plate wave device is formed upon a piezoelectric thin film formed from a piezoelectric material selected from among a group comprising at least one of the following types of materials: α-quartz, lithium niobate (LiNbO3), and lithium tantalate (LiTaO3) as well as Li2B4O7, AlPO4, GaPO4, langasite (La3Ga5SiO14), ZnO, and epitaxially grown (Al, Ga, In) nitrides.

13. The sensor of claim 1 wherein said piezoelectric thin film is formed by etching or deposition.

14. The sensor of claim 1 wherein said face shear wave bulk acoustic wave device is formed upon a piezoelectric substrate formed from a piezoelectric material selected from among a group comprising at least one of the following types of materials: CT or DT-cut α-quartz, lithium niobate (LINbO3), and lithium tantalate (LiTaO3) as well as Li2B4O7, AlPO4, GaPO4, langasite (La3Ga5SiO14), ZnO, and epitaxially grown (Al, Ga, In) nitrides.

15. The sensor of claim 1 wherein a vibration amplitude of the said flexural plate wave device is controlled by adjusting a power supplied to said flexural plate wave device.

16. The sensor of claim 1 wherein a vibration amplItude of said face shear wave bulk acoustic wave device is controlled by adjusting a power supplied to the said face shear wave bulk acoustic wave device.

17. A lubricity sensor, comprising:
a flexural plate wave device, wherein said flexural plate wave device comprises a membrane in which at least one inter-digital transducer (IDT) is formed upon in order to pump a flow of said liquid in a desired direction;
a face shear mode bulk acoustic wave device associated with and located proximate to said flexural plate wave device, wherein said face shear mode bulk acoustic wave device and said flexural plate wave device form a lubricity sensor wherein acoustic wave data produced by said flexural plate device together with said face shear mode bulk acoustic wave device when said lubricity sensor is exposed to a liquid relates directly to a lubricity of said liquid thereby providing lubricity measurement data associated with said liquid, wherein said flexural plate wave device and said race shear mode bulk acoustic wave device each operation in a low operating frequency range of approximately 0.1 MHz to 100 MHz; and
wherein said acoustic wave data comprises an amplitude and a phase veiocity associated with said flexural plate device and said shear mode device such that said amplitude and said phase velocity together provide an indication of said lubricity of said liquid.

18. The sensor of claim 17 wherein said acoustic wave data further comprises a frequency associated with said flexural plate device and said face shear mode bulk acoustic wave device such that said frequency provides an indication of said lubricity of said liquid.

19. The sensor of claim 17 wherein said acoustic wave data further comprises an oscillation gain compensation associated with said flexural plate device and said face shear mode bulk acoustic wave device such that said oscillation gain compensation provides an indication of said lubricity of said liquid.

20. A lubricity sensor, comprising:
a flexural plate wave device, wherein said flexural plate wave device comprises a membrane in which at least one inter-digital transducer (IDT) is formed upon in order to pump a flow of said liquid in a desired direction; and
a face shear mode bulk acoustic wave device associated with and located proximate to said flexural plate wave device, wherein said face shear mode bulk acoustic wave device and said flexural plate wave device form a lubricity sensor wherein acoustic wave data produced by said flexural plate device together with said face shear mode bulk acoustic wave device when said lubricity sensor is exposed to a liquid relates directly to a lubricity of said liquid thereby providing lubricity measurement data associated with said liquid,
wherein said acoustic wave data comprises an amplitude and a phase velocity associated with said flexural plate device and said shear mode device such that said amplitude and said phase velocity together provide an indication of said lubricity of said liquid;
wherein said acoustic wave data additionally comprises a frequency associated with said flexural plate device and said face shear mode bulk acoustic wave device such that said frequency provides an indication of said lubricity of said liquid;
wherein said acoustic wave data further comprises an oscillation gain compensation associated with said flexural plate device and said face shear mode bulk acoustic wave device such that said oscillation gain compensation provides an indication of said lubricity of said liquid;
wherein a vibration amplitude of the said flexural plate wave device is controlled by adjusting a power supplied to said flexural plate wave device; and
wherein a vibration amplitude of said face shear wave bulk acoustic wave device is controlled by adjusting a power supplied to the said face shear wave bulk acoustic wave device.

* * * * *

UNITED STATES PATENT AND TRADEMARK OFFICE
CERTIFICATE OF CORRECTION

PATENT NO. : 7,243,549 B2 Page 1 of 1
APPLICATION NO. : 11/132870
DATED : July 17, 2007
INVENTOR(S) : James ZT Liu et al.

It is certified that error appears in the above-identified patent and that said Letters Patent is hereby corrected as shown below:

Column 7, line 20, delete "amp1ltude" and add --amplitude--;
Column 7, line 45, delete "veiocity" and add --velocity--.

Signed and Sealed this

Sixth Day of November, 2007

JON W. DUDAS
*Director of the United States Patent and Trademark Office*